(12) United States Patent
Takami et al.

(10) Patent No.: US 11,446,077 B2
(45) Date of Patent: Sep. 20, 2022

(54) ENERGY SOURCE APPARATUS

(71) Applicant: Olympus Corporation, Hachioji (JP)

(72) Inventors: Sadayoshi Takami, Hachioji (JP); Yoshitaka Honda, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 364 days.

(21) Appl. No.: 16/560,196

(22) Filed: Sep. 4, 2019

(65) Prior Publication Data
US 2019/0388136 A1 Dec. 26, 2019

Related U.S. Application Data

(63) Continuation of application No. PCT/JP2017/009278, filed on Mar. 8, 2017.

(51) Int. Cl.
*A61B 18/12* (2006.01)
*A61B 18/10* (2006.01)
(Continued)

(52) U.S. Cl.
CPC .......... *A61B 18/10* (2013.01); *A61B 18/1445* (2013.01); *A61B 2018/00678* (2013.01);
(Continued)

(58) Field of Classification Search
CPC ..... A61B 18/08; A61B 18/10; A61B 18/1206; A61B 18/1445; A61B 2018/00678;
(Continued)

(56) References Cited

U.S. PATENT DOCUMENTS

2003/0073987 A1 4/2003 Sakurai et al.
2005/0101945 A1 5/2005 Sakurai et al.
(Continued)

FOREIGN PATENT DOCUMENTS

JP 2003116871 4/2003
JP 2009247893 10/2009
(Continued)

OTHER PUBLICATIONS

International Search Report and Written Opinion from corresponding International Application No. PCT/JP2017/009278, dated May 16, 2017.

*Primary Examiner* — Daniel W Fowler
(74) *Attorney, Agent, or Firm* — Oliff PLC

(57) ABSTRACT

A treatment system comprises a treatment tool and an energy source apparatus is used to electrically communicate with the treatment tool. The energy output source is configured to output high-frequency electric power to the bipolar electrodes so as to cause a high-frequency current to flow through a treatment target between the bipolar electrodes. A processor is used to control the energy output source. The processor performs an output control process on the heater electric power so that the heater reaches a target temperature and maintains at the target temperature. The processor detects a parameter related to the heater from the heater in the output control process based on the target temperature.

(Continued)

The processor sets a threshold value used to determine to stop or to lower the output to the bipolar electrodes while the treatment target is being modified by the high-frequency current applied thereto based on the detected parameter.

18 Claims, 5 Drawing Sheets

(51) Int. Cl.
  *A61B 18/14* (2006.01)
  *A61B 18/00* (2006.01)
(52) U.S. Cl.
  CPC ............ *A61B 2018/00702* (2013.01); *A61B 2018/00714* (2013.01); *A61B 2018/00791* (2013.01); *A61B 2018/00827* (2013.01); *A61B 2018/00875* (2013.01); *A61B 2018/00892* (2013.01)
(58) Field of Classification Search
  CPC .......... A61B 2018/00702; A61B 2018/00714; A61B 2018/00875; A61B 2018/00892; A61B 2018/00994
  See application file for complete search history.

(56) References Cited

U.S. PATENT DOCUMENTS

| | | |
|---|---|---|
| 2008/0172052 A1* | 7/2008 | Eder .................. A61B 18/1442 606/50 |
| 2009/0248002 A1 | 10/2009 | Takashino et al. |
| 2012/0136345 A1 | 5/2012 | Takashino |
| 2013/0338656 A1 | 12/2013 | Irisawa et al. |
| 2014/0148797 A1* | 5/2014 | Yasunaga ............... A61B 18/10 606/31 |
| 2015/0272657 A1* | 10/2015 | Yates ................ A61B 18/1206 606/34 |
| 2016/0310207 A1 | 10/2016 | Honda et al. |
| 2017/0252087 A1 | 9/2017 | Takashino et al. |
| 2018/0116709 A1 | 5/2018 | Honda et al. |

FOREIGN PATENT DOCUMENTS

| | | |
|---|---|---|
| JP | 5932187 | 5/2016 |
| WO | 2011018844 | 2/2011 |
| WO | 2013088891 | 6/2013 |
| WO | 2017018205 | 2/2017 |

\* cited by examiner

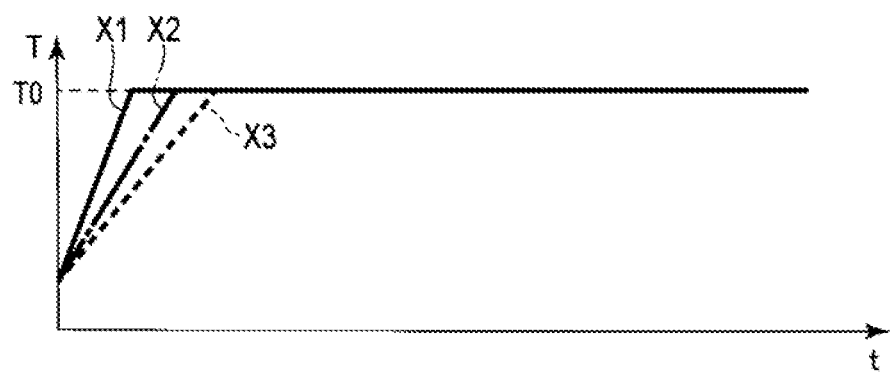
FIG. 5
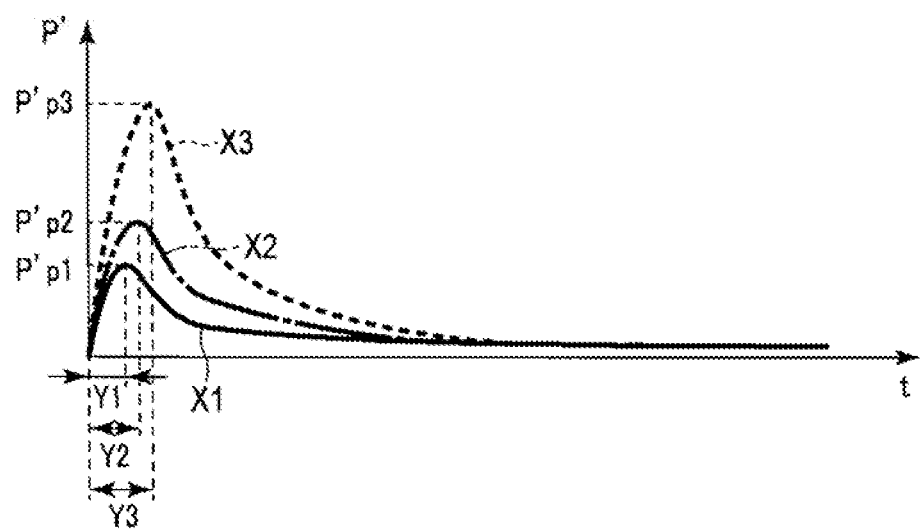

ENERGY SOURCE APPARATUS

CROSS-REFERENCE TO RELATED APPLICATION

This application is a continuation application of PCT Application No. PCT/JP 2017/009278 filed on Mar. 8, 2017, which is hereby incorporated by reference in its entirety.

TECHNICAL FIELD

The technology disclosed herein relates generally to an energy source apparatus, and more particularly, some embodiments relate to an energy source apparatus for use with a treatment tool having bipolar electrodes and a heater.

DESCRIPTION OF THE RELATED ART

US Patent Application Pub. No. 2009/0248002A1 discloses a treatment tool capable of gripping a treatment target such as a biotissue or the like between a pair of grippers and an energy source apparatus for supplying the treatment tool with electric energy. In the treatment tool, each of the grippers includes an electrode and at least one of the grippers includes a heater. The energy source apparatus outputs high-frequency electric power to the electrodes, i.e., bipolar electrodes, and outputs heater electric power to the heater. Consequently, a high-frequency current flows between the electrodes through the gripped treatment target and heat generated by the heater is applied to the gripped treatment target. In other words, both the high-frequency current and the heater heat are applied to the treatment target.

According to US Patent Application Pub. No. 2009/0248002A1, the energy source apparatus detects the state of the treatment target using the high-frequency electric power. The energy source apparatus controls the output of the high-frequency electric power based on the detected state of the treatment target. While both the high-frequency current and the heat are being applied to the treatment target, the heater heat may possibly affect the detection of the state of the treatment target using the high-frequency electric power. If the heater heat affects the detection of the state using the high-frequency electric power, then the heater heat also affects the control of the output of the high-frequency electric power based on the state of the treatment target.

BRIEF SUMMARY OF EMBODIMENTS

The disclosed technology has been made in view of the foregoing.

One aspect of the disclosed technology is directed a treatment system comprises a treatment tool having a heater and bipolar electrodes to grip a treatment target. An energy source apparatus is used to electrically communicate with the treatment tool. The energy output source is configured to output high-frequency electric power to the bipolar electrodes so as to cause a high-frequency current to flow through a treatment target between the bipolar electrodes. The energy output source is configured to output heater electric power to the heater so as to cause the heater to generate heat. At least one processor is used to control the energy output source. The processor performs an output control process on the heater electric power so that the heater reaches a target temperature and maintains the heater at the target temperature. The processor detects a parameter related to the heater from the heater in the output control process based on the target temperature. The processor sets a threshold value used to determine to stop or to lower the output to the bipolar electrodes based on the parameter.

Another aspect of the disclosed technology is directed to a method of operating a treatment system. The treatment system includes a treatment tool having a heater and bipolar electrodes to grip a treatment target. An energy source apparatus is used to electrically communicate with the treatment tool. The energy source apparatus comprises at least one processor used to control the energy output source. The processor is performing an output control process on the heater electric power so that the heater reaches a target temperature and maintains the heater at the target temperature. Next, the processor is detecting a parameter related to the heater from the heater in the output control process based on the target temperature. And finally, the processor is setting a threshold value used to determine to stop or to lower the output to the bipolar electrodes while the treatment target is being modified by the high-frequency current applied thereto, based on the detected parameter.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 4 is a schematic diagram illustrating an example of chronological changes in the temperature of a heater in the processing sequence carried out by the processor according to the first embodiment.

FIG. 5 is a schematic diagram illustrating an example of chronological changes in the heater electric power output from a heater power supply when the temperature of the heater changes chronologically as illustrated in FIG. 4 according to the first embodiment.

DETAILED DESCRIPTION OF THE EMBODIMENTS

In the following description, various embodiments of the technology will be described. For purposes of explanation, specific configurations and details are set forth in order to provide a thorough understanding of the embodiments.

However, it will also be apparent to one skilled in the art that the technology disclosed herein may be practiced without the specific details. Furthermore, well-known features may be omitted or simplified in order not to obscure the embodiment being described.

It is an object of the present disclosure to provide an energy source apparatus that appropriately detects the state of a treatment target even while outputting both high-frequency electric power and heater electric power to a treatment tool, and appropriately controls the output of the high-frequency electric power based on the state of the treatment target.

First Embodiment

A first embodiment of the present disclosure will be described below with reference to FIGS. 1 through 7.

Figure 1:
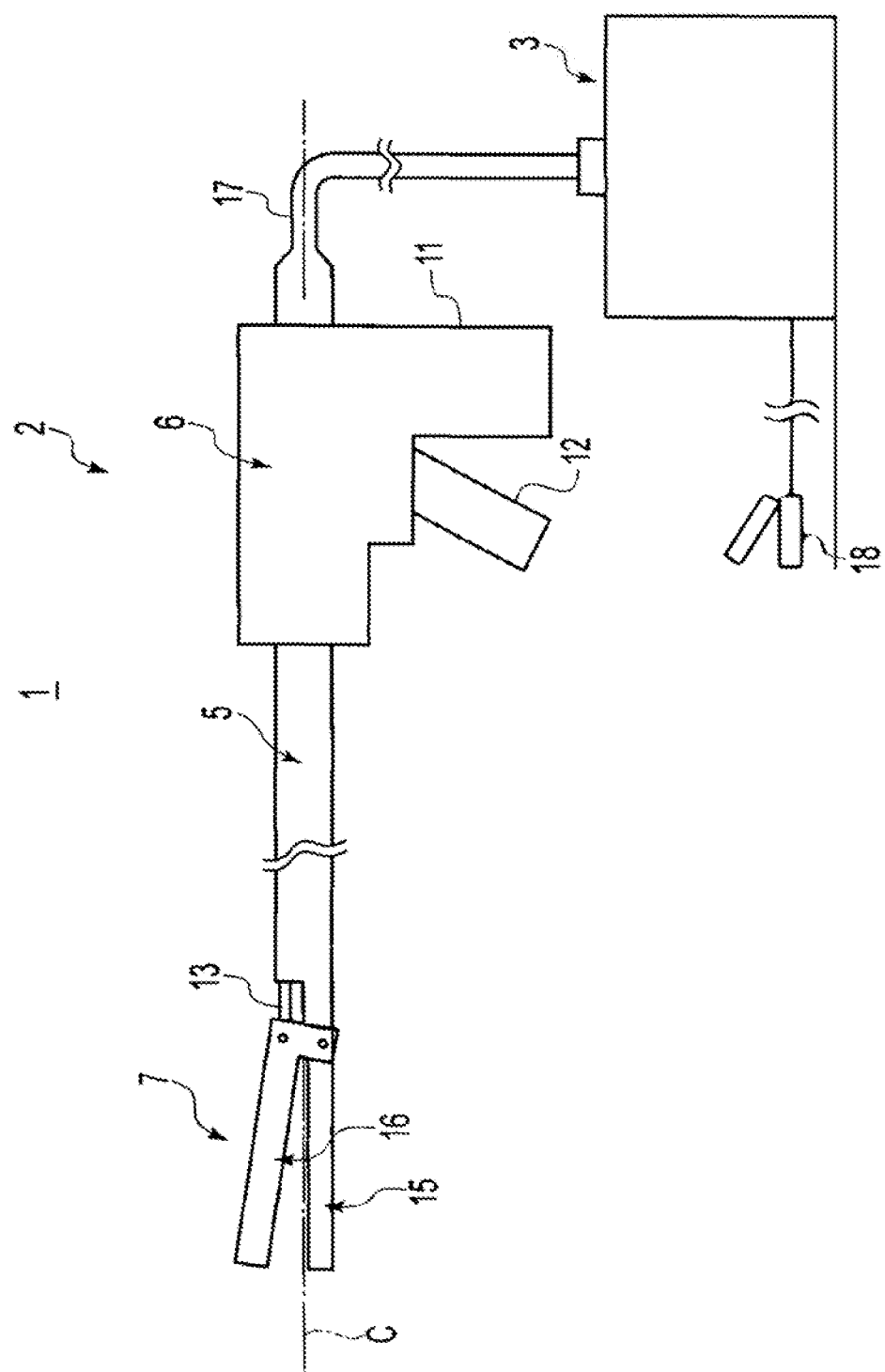
FIG. 1 is a schematic view illustrating a treatment system according to a first embodiment.

FIG. 1 is a view illustrating a treatment system 1 according to the present embodiment. As illustrated in FIG. 1, the treatment system 1 includes a treatment tool 2 and an energy source apparatus 3 for supplying the treatment tool 2 with electric energy. When the treatment tool 2 is in use, the energy source apparatus 3 is used together with the treatment tool 2. The treatment tool 2 includes a shaft 5 having a longitudinal axis C as its central axis. A housing 6 that can be held is coupled to an end, i.e., proximal end, of the shaft 5 in a direction along the longitudinal axis C. An end effector 7 is disposed on the end of the shaft 5 that is opposite to the end where the housing 6 is positioned, i.e., on a distal end of the shaft 5. The housing 6 includes a grip 11 and a handle 12 mounted angularly movably thereon. When the handle 12 is angularly moved with respect to the housing 6, the handle 12 is opened or closed with respect to the grip 11.

The end effector 7 includes a pair of grippers 15 and 16. In the treatment tool 2, a movable member 13 extends along the longitudinal axis C inside or outside of the shaft 5. The movable member 13 has an end, i.e., distal end, connected to the end effector 7. The other end, i.e., proximal end, of the movable member 13 is coupled to the handle 12 in the housing 6. When the handle 12 is opened or closed with respect to the grip 11, the movable member 13 moves along the longitudinal axis C of the shaft 5, opening or closing the grippers 15 and 16. The grippers 15 and 16 are thus capable of gripping a biotissue such as a blood vessel or the like as a treatment target therebetween. According to an embodiment, one of the grippers 15 and 16 is integral with or fixed to the shaft 5, whereas the other of the grippers 15 and 16 is angularly movably mounted on a distal end of the shaft 5. According to another embodiment, both the grippers 15 and 16 are angularly movably mounted on the distal end of the shaft 5. According to an embodiment, an operating member, not illustrated, such as a rotary knob or the like, is mounted on the housing 6. When the operating member is rotated with respect to the housing 6, the shaft 5 and the end effector 7 are rotated about the longitudinal axis C with respect to the housing 6.

A cable 17 has an end connected to the housing 6. The other end of the cable 17 is separably connected to the energy source apparatus 3. The treatment system 1 includes a foot switch 18 as an operating member separate from the treatment tool 2. The foot switch 18 is electrically connected to the energy source apparatus 3. The foot switch 18 inputs an operation for causing the energy source apparatus 3 to output electric energy to the treatment tool 2. According to an embodiment, an operating button or the like that is mounted as an operating member on the housing 6 is included instead of or in addition to the foot switch 18. The energy source apparatus 3 outputs electric energy to the treatment tool 2 in response to an operation entered through the operating member.

Figure 2:
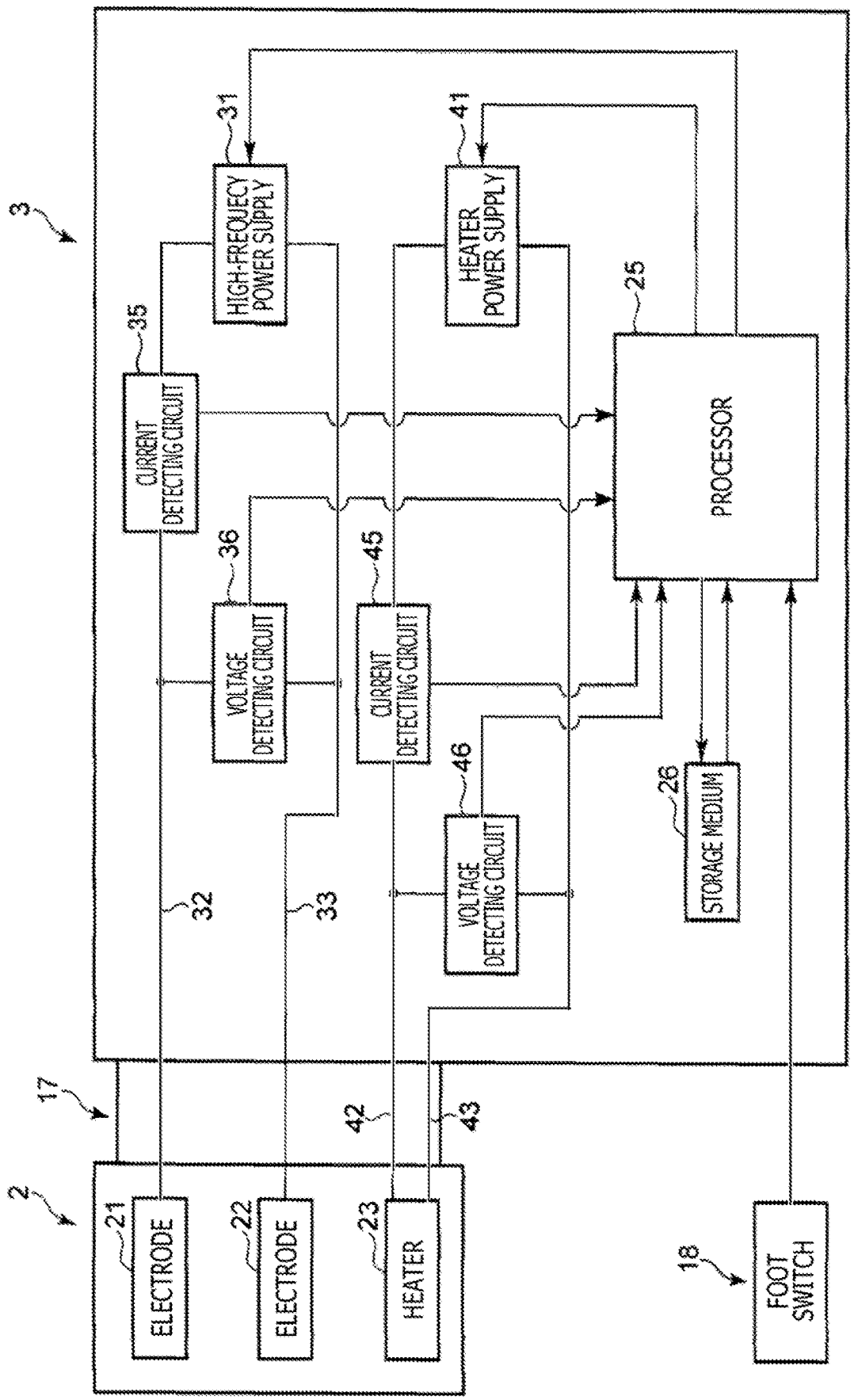
FIG. 2 is a block diagram schematically illustrating an arrangement for supplying electric energy from an energy source apparatus according to the first embodiment to a treatment tool.

FIG. 2 is a diagram illustrating an arrangement for supplying electric energy, i.e., high-frequency electric power P and heater electric power P' to be described hereinafter according to the present embodiment, from the energy source apparatus 3 to the treatment tool 2. As illustrated in FIG. 2, the treatment tool 2 includes an electrode 21 on the gripper 15 and an electrode 22 on the gripper 16. The electrodes 21 and 22 are bipolar electrodes included in the end effector 7. The end effector 7 includes a heater 23 as a heat generating element disposed on at least one of the grippers 15 and 16.

The energy source apparatus 3 includes a processor, i.e., controller, 25 and a storage medium 26. The processor 25 is in the form of an integrated circuit or the like including a central processing unit (CPU), an application specific integrated circuit (ASIC), a field programmable gate array (FPGA), or the like. The energy source apparatus 3 may include only one processor 25 or a plurality of processors 25. The processor 25 carries out a processing sequence according to programs stored in the processor 25 or the storage medium 26. The storage medium 26 stores processing programs used by the processor 25, parameters, functions, and tables used in operations performed by the processor 25, and so on. The processor 25 detects whether or not an operation is entered through the operating member such as the foot switch 18 or the like.

The energy source apparatus 3 includes a high-frequency power supply 31 as an energy output source. The high-frequency power supply 31 includes a waveform generator, a converting circuit, a transformer, and so on. The high-frequency power supply 31 converts electric power from a battery power supply, an outlet power supply, or the like into high-frequency electric power P. The high-frequency power supply 31 is electrically connected to the electrode 21 on the gripper 15 through an electric supply path 32. The high-frequency power supply 31 is also electrically connected to the electrode 22 on the griper 16 through an electric supply path 33. Each of the electric supply paths 32 and 33 extends in the cable 17, the housing 6, and the shaft 5. Each of the electric supply paths 32 and 33 is in the form of an electric wire or the like. The high-frequency power supply 31 is capable of outputting the converted high-frequency electric power P. While the treatment target is being gripped between the grippers 15 and 16, the high-frequency electric power P output from the high-frequency power supply 31 is supplied through the electric supply paths 32 and 33 to the electrodes 21 and 22. Therefore, a high-frequency current flows through the treatment target between the electrodes, i.e., bipolar electrodes 21 and 22. At this time, the electrodes 21 and 22 have respective potentials that are different from each other. When a high-frequency current having a certain magnitude is applied as treatment energy to the treatment target, the treatment target is modified by the heat caused by the high-frequency current. When an operation is entered through the foot switch 18 or the like, the processor 25 controls the output from the high-frequency power supply 31 to the electrodes 21 and 22 in a manner to be described hereinafter.

The electric paths through which the high-frequency electric power P is output from the high-frequency power supply 31 to the electrodes 21 and 22 include a current detecting circuit 35 and a voltage detecting circuit 36. While the high-frequency electric power P is being output from the high-frequency power supply 31, the current detecting circuit 35 detects the current value of an output current I from the high-frequency power supply 31. At the same time, the voltage detecting circuit 36 detects the voltage value of an output voltage V from the high-frequency power supply 31. An analog signal representing the current value detected by the current detecting circuit 35 and an analog signal representing the voltage value detected by the voltage detecting circuit 36 are converted into digital signals by analog-digital (A/D) converters, not illustrated, or the like. The converted digital signals are transmitted to the processor 25. The processor 25 now acquires information regarding the output current I and the output voltage V from the high-frequency power supply 31. Based on the output current I and the output voltage V that have been acquired, the processor 25 detects impedances of the electric paths through which the high-frequency electric power P is output from the high-frequency power supply 31 to the electrodes 21 and 22. Based on the impedances of the electric paths for the high-frequency electric power P, the processor 25 detects an impedance Z of the gripped treatment target, i.e., a tissue impedance. Based on the output current I and the output voltage V that have been acquired, the processor 25 also detects an electric power value of the high-frequency electric power P, i.e., an electric power value of the output electric power from the high-frequency power supply 31 to the electrodes 21 and 22. The processor 25 controls the output from the high-frequency power supply 31 using the output current I and the output voltage V that have been acquired, and the impedance Z and the high-frequency electric power P that have been detected, in a manner to be described hereinafter.

The energy source apparatus 3 includes a heater power supply 41 as an energy output source. The heater power supply 41 includes a converting circuit, a transformer, and so on. The heater power supply 41 converts electric power from a battery power supply, an outlet power supply, or the like into heater electric power P'. The heater power supply 41 is electrically connected to the heater 23 through electric supply paths 42 and 43. Each of the electric supply paths 42 and 43 extends in the cable 17, the housing 6, and the shaft 5. Each of the electric supply paths 42 and 43 is in the form of an electric wire or the like. The heater power supply 41 is capable of outputting the converted heater electric power P'. The heater electric power P' that is output is direct current (DC) electric power or alternate current (AC) electric power. When the heater electric power P' output from the heater power supply 41 is supplied through the electric supply paths 42 and 43 to the heater 23, the heater 23 generates heat. While the treatment target is being gripped between the grippers 15 and 16, the heat generated by the heater 23 is applied to the treatment target. When a certain amount of heater heat is applied as treatment energy to the treatment target, the treatment target is modified. When an operation is entered through the foot switch 18 or the like, the processor 25 controls the output from the heater power supply 41 to the heater 23 in a manner to be described hereinafter.

The electric paths through which the heater electric power P' is output from the heater power supply 41 to the heater 23 include a current detecting circuit 45 and a voltage detecting circuit 46. While the heater electric power P' is being output from the heater power supply 41, the current detecting circuit 45 detects the current value of an output current I' from the heater power supply 41. At the same time, the voltage detecting circuit 46 detects the voltage value of an output voltage V' from the heater power supply 41. An analog signal representing the current value detected by the current detecting circuit 45 and an analog signal representing the voltage value detected by the voltage detecting circuit 46 are converted into digital signals by A/D converters, not illustrated, or the like. The converted digital signals are transmitted to the processor 25. The processor 25 now acquires information regarding the output current I' and the output voltage V' from the heater power supply 41. Based on the output current I' and the output voltage V' that have been acquired, the processor 25 detects impedances of the electric paths through which the heater electric power P' is output from the heater power supply 41 to the heater 23. Based on the impedances of the electric paths for the heater electric power P', the processor 25 detects a resistance R of the heater 23. The resistance R of the heater 23 varies depending on a temperature T of the heater 23. The storage medium 26 or the like stores a function, a table, or the like that represents the relationship between the temperature T and the resistance R of the heater 23. Based on the detected resistance R and the stored relationship between the temperature T and the resistance R, the processor 25 detects the temperature T of the heater 23. Based on the output current I' and the output voltage V' that have been acquired, the processor 25 also detects an electric power value of the heater electric power P', i.e., an electric power value of the output electric power from the heater power supply 41 to the heater 23. The processor 25 controls the output from the high-frequency power supply 31 and the output from the heater power supply 41 using the output current I' and the output voltage V' that have been acquired and the temperature T, i.e., the resistance R, and the heater electric power P' that have been detected, in a manner to be described hereinafter.

Next, operation and advantages of the energy source apparatus 3 and the treatment system 1 will be described below. For performing a treatment using the treatment system 1, the treatment tool 2 is connected through the cable 17 to the energy source apparatus 3. The surgeon holds the housing 6 and inserts the end effector 7 into a body cavity such as an abdominal cavity or the like. While a treatment target such as a biotissue or the like is being positioned between the grippers 15 and 16, the surgeon closes the handle 12 on the grip 11. The grippers 15 and 16 are now closed, gripping the treatment target therebetween. When the surgeon enters an operation through the operating member such as the foot switch 18 or the like while the treatment target is being gripped, the output from the high-frequency power supply 31 to the electrodes 21 and 22 and the output from the heater power supply 41 to the heater 23 are controlled. When the high-frequency electric power P is supplied to the electrodes 21 and 22, a high-frequency current flows through the treatment target as described hereinbefore. When the heater electric power P' is supplied to the heater 23, heat generated by the heater 23 is applied to the treatment target. The treatment target is treating using the high-frequency current and the heater heat as treatment energy.

Figure 3:
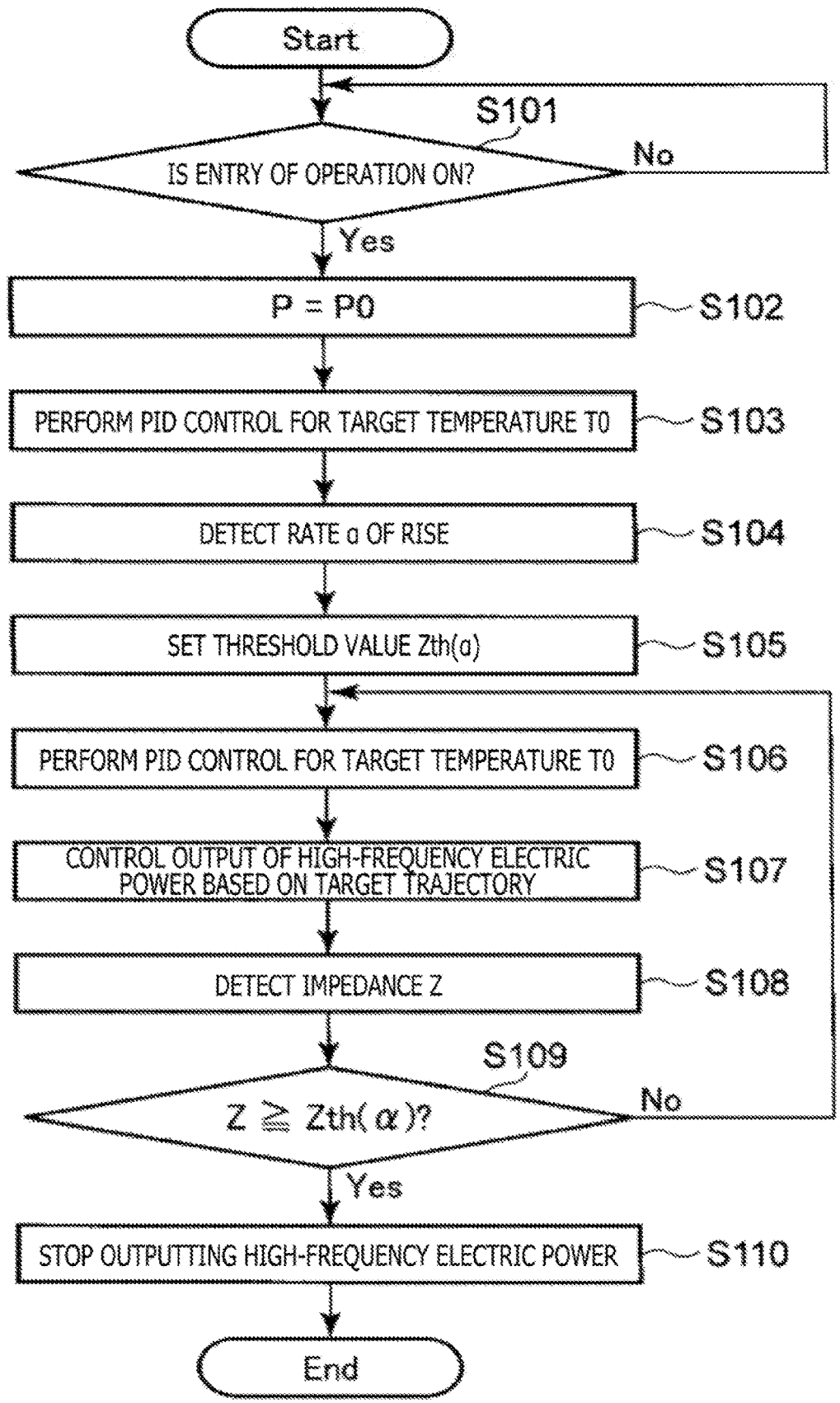
FIG. 3 is a flowchart of a processing sequence carried out by a processor of the energy source apparatus according to the first embodiment.

FIG. 3 is a flowchart of a processing sequence carried out by the processor 25 of the energy source apparatus 3. As illustrated in FIG. 3, the processor 25 determines whether or not an operation is entered through the operating member such as the foot switch 18 or the like, i.e., whether the entry of an operation is ON or OFF (S101). If an operation is not entered (S101—No), then processing returns to S101. In other words, the processor 25 waits until an operation is entered through the operating member. If an operation is entered through the operating member (S101—Yes), then the processor 25 starts to output the high-frequency electric power P from the high-frequency power supply 31 to the electrodes 21 and 22 and also starts to output the heater electric power P' from the heater power supply 41 to the heater 23. According to the present embodiment, when the high-frequency electric power P starts to be output, the processor 25 outputs the high-frequency electric power P from the high-frequency power supply 31 at an electric power value that is constant as a fixed value P0 (S102). At this time, the output current I and the output voltage V from the high-frequency power supply 31 are adjusted to keep the electric power value of the output electric power from the high-frequency power supply 31 constant as the fixed value P0.

When the heater electric power P' starts to be output from the heater power supply 41, the processor 25 performs a proportional-integral-derivative (PID) control process for a target temperature T0 on the output from the heater power supply 41 to the heater 23 (S103). Specifically, an output control process is carried out on the output to the heater 23 for causing the temperature T of the heater 23 to reach the target temperature T0 and maintaining the temperature T of the heater 23 at the target temperature T0. According to the PID control process for the target temperature T0, the processor 25 detects the resistance R of the heater 23 based on the output current I' and the output voltage V' from the heater power supply 41 and detects the temperature T of the heater 23 based on the detected resistance R, as described hereinbefore. Then, the processor 25 adjusts the output electric power, i.e., the heater electric power P', the output current I', and the output voltage V' to the heater 23, based on the temperature deviation between the target temperature T0 and the temperature T of the heater 23, a time integral value of the temperature deviation, i.e., an integrated value of the temperature deviation, and a time differential value of the temperature deviation, i.e., a time rate of change of the temperature deviation, causing the temperature T to reach the target temperature T0 and maintaining the temperature T at the target temperature T0. For example, if the temperature deviation between the target temperature T0 and the temperature T is large, then the processor 25 causes the heater power supply 41 to output the heater electric power P' at a large electric power value. If the temperature deviation between the target temperature T0 and the temperature T is small, and the temperature deviation is zero, then the processor 25 causes the heater power supply 41 to output the heater electric power P' at a small electric power value.

In an output control process for controlling the output from the heater power supply 41 to the heater 23 based on the target temperature T0, the processor 25 detects a chronological rate $\alpha$ of rise of the temperature T up to the target temperature T0 as a parameter related to the temperature T of the heater 23 (S104). The rate $\alpha$ of rise of the temperature T varies depending on a tissue volume of the treatment target including the thickness of a blood vessel, etc., the degree of wetness of the treatment target, and so on. In other words, the rate $\alpha$ of rise, i.e., the speed of rise, varies depending on the state of the treatment target including a thermal load on the treatment target. The thermal load on the treatment target represents how difficult it is for the temperature of the treatment target to rise. Providing identical amounts of heat are applied to the treatment target, the temperature of the treatment target is more difficult to rise under a larger thermal load. The processor 25 sets a threshold value Zth($\alpha$) for the impedance Z that is used to determine whether to stop output from the high-frequency power supply 31 to the electrodes 21 and 22, based on the rate $\alpha$ of rise detected as a parameter (S105). At this time, the threshold value Zth($\alpha$) is calculated using the detected rate $\alpha$ of rise and a function or table, stored in the storage medium 26 or the like, representing the relationship between rates $\alpha$ of rise of the temperature T and the threshold value Zth for the impedance Z. According to the present embodiment, the threshold value Zth for the impedance Z is set such that the smaller the rate $\alpha$ of rise of the temperature T is, the larger the threshold value Zth for the impedance Z. In one embodiment, the threshold value Zth is an absolute value relative to zero. In another embodiment, the processor 25 detects an initial value Ze for the impedance Z at the same time as or immediately after the start of output from the high-frequency power supply 31. The processor 25 sets the threshold value Zth as a relative value with respect of the initial value Ze. After the rate $\alpha$ of rise of the temperature T has been calculated and the threshold value Zth for the impedance Z has been set, the processor 25 performs the above PID control process for the target temperature T0 on the output from the heater power supply 41 to the heater 23 (S106).

When the rate $\alpha$ of rise of the temperature T is detected, the processor 25 sets a target trajectory that increases chronologically at a constant rate $\beta$ of increase for the impedance Z of the treatment target. Then, the processor 25 switches the output from the high-frequency power supply 31 to a state in which the impedance Z changes along the target trajectory. In other words, the processor 25 controls the output from the high-frequency power supply 31 to the electrodes 21 and 22 into a state in which the impedance Z changes chronologically along the target trajectory with the rate $\beta$ of increase (S107). At this time, the output electric power, i.e., the high-frequency electric power P', the output current I, and the output voltage V from the high-frequency power supply 31 are adjusted to a state in which the impedance Z changes at the constant rate $\beta$ of increase. According to the present embodiment, the processor 25 sets the rate $\beta$ of increase, which is a target value of the target trajectory for the impedance Z, to a fixed value $\beta$0. While the output of the high-frequency electric power P is being controlled based on the target trajectory for the impedance Z, the treatment target is modified by the high-frequency current applied thereto. Furthermore, while the output of the high-frequency electric power P is being controlled based on the target trajectory for the impedance Z, the processor 25 detects the impedance Z based on the output current I and the output voltage V from the high-frequency power supply 31 (S108). If the high-frequency current is continuously applied to the treatment target that has been dehydrated to a certain extent, then the impedance Z increases chronologically due to the heat caused by the high-frequency current. According to the present embodiment, moreover, at a point of time upon elapse of a certain time from the start of the output control process for controlling the output from the high-frequency power supply 31 based on the target trajectory for the impedance Z, the treatment target is dehydrated to a certain extent due to the heater heat and the heat caused by the high-frequency current. Therefore, after the point of time upon elapse of the certain period of time from the start of the output control process for controlling the output from the high-frequency power supply 31 based on the target trajectory for the impedance Z, the impedance Z increases chronologically due to the continuously applied high-frequency current.

While the output of the high-frequency electric power P is being controlled based on the target trajectory for the impedance Z, the processor 25 detects whether or not the detected impedance Z is equal to or larger than a threshold value Zth($\alpha$) that has been set (S109). If the impedance Z is smaller than the threshold value Zth($\alpha$) (S109—No), then processing goes back to S106. Then, the steps from S106 are successively carried out. Therefore, the processor 25 continues the output from the high-frequency power supply 31 to the electrodes, i.e., bipolar electrodes, 21 and 22, continuously modifying the treatment target with the application of the high-frequency current thereto, until the impedance Z reaches the threshold value Zth($\alpha$), i.e., until a condition based on the set threshold value Zth($\alpha$) is satisfied. If the impedance Z is equal to or larger than the threshold value Zth($\alpha$) (S109—Yes), then the processor 25 stops the output from the high-frequency power supply 31 to the electrodes 21 and 22 (S110). At this time, the processor 25 may stop the output from the heater power supply 41 to the heater 23 in response to the stoppage of the output to the electrodes 21 and 22, or may continue the output from the heater power supply 41 to the heater 23. If the output to the heater 23 is continued, then the processor 25 stops the output from the heater power supply 41 upon elapse of a certain time from the stoppage of the output to the electrodes 21 and 22 or based on an operation entered by the surgeon or the like. In case the output to the heater 23 is continued, the processor 25 does not need to continue the PID control process for the target temperature T0. For example, in response to the stoppage of the output to the electrodes 21 and 22, the processor 25 may control the output of the heater electric power P' to the heater 23 to lower the temperature T of the heater 23 to a target temperature Ta0 lower than the target temperature T0 and maintain the temperature T of the heater 23 at the target temperature Ta0. In this case, the target temperature Ta0 is set to a temperature low enough not to modify the treatment target, for example.

Figure 6:
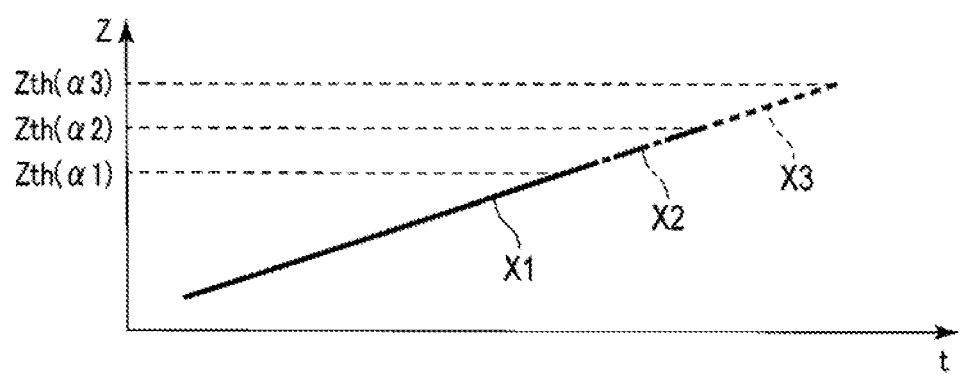
FIG. 6 is a schematic diagram illustrating an example of target trajectories for an impedance set when the temperature of the heater changes chronologically as illustrated in FIG. 4 according to the first embodiment.
Figure 7:
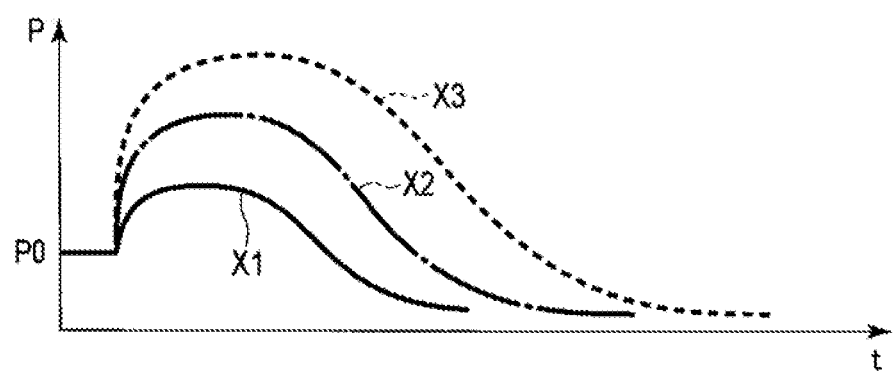
FIG. 7 is a schematic diagram illustrating an example of chronological changes in the high-frequency electric power output from a high-frequency power supply when the temperature of the heater changes chronologically as illustrated in FIG. 4 according to the first embodiment.

FIG. 4 illustrates an example of chronological changes in the temperature T of the heater 23 in the processing sequence carried out by the processor 25 as described hereinbefore. FIG. 5 illustrates an example of chronological changes in the heater electric power P' output from the heater power supply 41 to the heater 23 when the temperature T of the heater 23 changes chronologically as illustrated in FIG. 4. FIG. 6 illustrates an example of target trajectories for the impedance Z set when the temperature T of the heater 23 changes chronologically as illustrated in FIG. 4. FIG. 7 illustrates an example of chronological changes in the high-frequency electric power P output from the high-frequency power supply 31 to the electrodes 21 and 22 when the temperature T of the heater 23 changes chronologically as illustrated in FIG. 4. In each of FIGS. 4 through 7, a horizontal axis represents time t from the start, used as a reference, of the output from the heater power supply 41. In FIG. 4, a vertical axis represents the temperature T of the heater 23. In FIG. 5, a vertical axis represents the heater electric power P'. In FIG. 6, a vertical axis represents the impedance Z of the treatment target. In FIG. 7, a vertical axis represents the high-frequency electric power P. Each of FIGS. 4 through 7 illustrates the chronological changes in three states, i.e., tissue states, X1 through X3. The states X1 through X3 indicate thermal loads on the treatment target that are different from each other due to the tissue volume of the treatment target and/or the degree of wetness of the treatment target. In the state X1, the tissue volume of the treatment target is smaller because the blood vessel as the treatment target is thin, etc., and/or the treatment target is drier, than in the state X2. Therefore, the thermal load on the treatment target is smaller in the state X1 than in the state X2. In the state X3, the tissue volume of the treatment target is larger because the blood vessel as the treatment target is thick, etc., and/or the treatment target is wetter, than in the state X2. Therefore, the thermal load on the treatment target is larger in the state X3 than in the state X2. In each of FIGS. 4 through 7, the chronological changes in the state X1 are indicated by the solid-line curve, the chronological changes in the state X2 by the dot-and-dash-line curve, and the chronological changes in the state X3 by the broken-line curve.

When the PID control process is performed on the output from the heater power supply 41 for the target temperature T0, as described hereinbefore, the larger the thermal load on the treatment target, the smaller the rate $\alpha$ of rise of the temperature T up to the target temperature T0. In the examples illustrated in FIGS. 4 through 7, actually, the rate $\alpha 1$ of rise of the temperature T in the state X1 is larger than the rate $\alpha 2$ of rise of the temperature T in the state X2, and the rate $\alpha 3$ of rise of the temperature T in the state X3 is smaller than the rate $\alpha 2$ of rise of the temperature T in the state X2.

When the PID control process is performed for the target temperature T0, until the temperature T becomes close to the target temperature T0 to a certain extent after the heater electric power P' has started to be output, since the temperature deviation between the target temperature T0 and the temperature T is large, the processor 25 increases the output from the heater power supply 41. Consequently, the heater electric power P' increases chronologically until the temperature T becomes close to the target temperature T0 to a certain extent. When the temperature T becomes close to the target temperature T0 to a certain extent, the temperature deviation between the target temperature T0 and the temperature T becomes small. It is also necessary to prevent the temperature T from overshooting the target temperature T0. Therefore, when the temperature T becomes close to the target temperature T0 to a certain extent, the processor 25 reduces the output from the heater power supply 41. Consequently, when the temperature T becomes close to the target temperature T0 to a certain extent, the heater electric power P' decreases chronologically. As the heater electric power P' changes chronologically as described hereinbefore, until the temperature T reaches the target temperature T0 after the temperature T has become close to the target temperature T0 to a certain extent, e.g., immediately before the temperature T reaches the target temperature T0, the heater electric power P' becomes peak electric power P'p. At the time the heater electric power P' has become the peak electric power P'p, the heater electric power P' switches from a chronologically increasing state to a chronologically decreasing state.

When the PID control process is performed on the output from the heater power supply 41 for the target temperature T0, as described hereinbefore, the larger the thermal load on the treatment target, the higher the output from the heater power supply 41. Therefore, the larger the thermal load on the treatment target, the larger the peak electric power P'p of the heater electric power P. In the examples illustrated in FIGS. 4 through 7, actually, the peak electric power P'p1 of the heater electric power P' in the state X1 is smaller than the peak electric power P'p2 of the heater electric power P' in the state X2, and the peak electric power P'p3 of the heater electric power P' in the state X3 is larger than the peak electric power P'p2 of the heater electric power P' in the state X2. Prior to the point of time at which the heater electric power P' has decreased from the peak electric power P'p to a certain extent, the larger the thermal load on the treatment target, the larger an integrated value W' of the heater electric power P' between two points of time, as is the case with the peak electric power P'p. For example, the larger the thermal load on the treatment target, the larger the integrated value of the heater electric power P' until it reaches the peak electric power P'p after it has started to be output. Inasmuch as the larger the thermal load on the treatment target, the smaller the rate α of rise of the temperature T, a time Y required for the heater electric power P' to reach the peak electric power P'p after it has started to be output is long. In the examples illustrated in FIGS. 4 through 7, actually, a time Y1 required for the heater electric power P' to reach the peak electric power P'p1 in the state X1 is shorter than a time Y2 required for the heater electric power P' to reach the peak electric power P'p2 in the state X2, and a time Y3 required for the heater electric power P' to reach the peak electric power P'p3 in the state X3 is longer than the time Y2 required for the heater electric power P' to reach the peak electric power P'p2 in the state X2.

In case the thermal load on the treatment target is small because the tissue volume is small, etc., the temperature T of the heater 23 rises even though the heater electric power P' that is output is small to a certain degree. Therefore, in case the thermal load on the treatment target is small, the heater electric power P' increases gradually until it reaches the peak electric power P'p immediately after it has started to be output according to the PID control process for the target temperature T0. Even after the heater electric power P' has reached the peak electric power P'p, the heater electric power P' decreases gradually. On the other hand, in case the thermal load on the treatment target is large because the tissue volume is large, etc., it is difficult for the temperature T of the heater 23 to rise unless the heater electric power P' that is output is increased to a certain extent. Therefore, in case the thermal load on the treatment target is large, the heater electric power P' increases quickly until it reaches the peak electric power P'p immediately after it has started to be output according to the PID control process for the target temperature T0. After the heater electric power P' has reached the peak electric power P'p, the processor 25 quickly reduces the heater electric power P' in order to prevent the temperature T from overshooting the target temperature T0. As the heater electric power P' varies depending on the thermal load on the treatment target, as described hereinbefore, the larger the thermal load on the treatment target, the larger a rate γ of increase of the heater electric power P' up to the peak electric power P'p. Furthermore, the larger the thermal load on the treatment target, the larger a rate ε of reduction of the heater electric power P' after having reached the peak electric power P'p. In the examples illustrated in FIGS. 4 through 7, actually, the rate γ1 of increase of the heater electric power P' in the state X1 is smaller than the rate γ2 of increase of the heater electric power P' in the state X2, and the rate γ3 of increase of the heater electric power P' in the state X3 is larger than the rate γ2 of increase of the heater electric power P' in the state X2. The rate ε1 of reduction of the heater electric power P' in the state X1 is smaller than the rate ε2 of reduction of the heater electric power P' in the state X2, and the rate ε3 of reduction of the heater electric power P' in the state X3 is larger than the rate ε2 of reduction of the heater electric power P' in the state X2.

Moreover, since the larger the thermal load on the treatment target, the smaller the rate α of rise of the temperature T, the processor 25 sets the threshold value Zth for the impedance Z that is used to determine whether to stop the output to the electrodes 21 and 22, to a larger value. Actually, the threshold value Zth(α1) for the impedance Z set in the state X1 is smaller than the threshold value Zth(α2) for the impedance Z set in the state X2. Furthermore, the threshold value Zth(α3) for the impedance Z set in the state X3 is larger than the threshold value Zth(α2) for the impedance Z set in the state X2.

According to the present embodiment, as described hereinbefore, when the rate α of rise of the temperature T is detected, the processor 25 performs the output control process for controlling the output of the high-frequency electric power P based on the target trajectory where the impedance Z increases at the constant rate β of increase, i.e., a fixed value β0. In the output control process for controlling the output of the high-frequency electric power P based on the target trajectory for the impedance Z, the larger the set threshold value Zth(α), the longer the time required for the impedance Z to reach the threshold value Zth(α). Therefore, according to a control process for stopping the output of the high-frequency electric power P based on the arrival of the impedance Z at the threshold value Zth(α), the larger the set threshold value Zth(α), the longer the time until the output from the high-frequency power supply 31 is stopped and the longer the time during which the output is produced from the high-frequency power supply 31. Consequently, the larger the set threshold value Zth(α), the longer the time during which the high-frequency current is applied to the treatment target. In the examples illustrated in FIGS. 4 through 7, actually, the time during which the output is produced from the high-frequency power supply 31 in the state X1 is shorter than the time during which the output is produced from the high-frequency power supply 31 in the state X2. The time during which the output is produced from the high-frequency power supply 31 in the state X3 is longer than the time during which the output is produced from the high-frequency power supply 31 in the state X2.

The larger the thermal load on the treatment target is, the larger the high-frequency electric power P that is output is, in the output control process for controlling the output of the high-frequency electric power P based on the target trajectory for the impedance Z described hereinbefore. Therefore, In the output control process for controlling the output of the high-frequency electric power P based on the target trajectory for the impedance Z, the larger the thermal load on the treatment target, the larger the high-frequency current flowing through the treatment target. In the examples illustrated in FIGS. 4 through 7, actually, in the output control process for controlling the output of the high-frequency electric power P based on the target trajectory for the impedance Z, the high-frequency electric power P that is output is smaller in the state X1 than in the state X2, and the high-frequency electric power P that is output is larger in the state X3 than in the state X2. In the output control process for controlling the output of the high-frequency electric power P based on the target trajectory for the impedance Z, the high-frequency electric power P that is output increases chronologically while the impedance Z is being low. When the impedance Z rises to a certain extent, the high-frequency electric power P that is output switches from a chronologically increasing state to a chronologically decreasing state. Until the output of the high-frequency electric power P is stopped, the high-frequency electric power P decreases chronologically. In the examples illustrated in FIGS. 4 through 7, before the rate α of rise is detected, the output from the high-frequency power supply 31 is controlled to keep the electric power value of the high-frequency electric power P constant as the fixed value P0 in either one of the states X1 through X3.

According to the present embodiment, as described hereinbefore, the control process for controlling the output to the heater 23 is carried out to cause the heater 23 to reach the target temperature T0 and to keep the heater 23 at the target temperature T0. In the control process based on the target temperature T0, the rate α of rise until the temperature T reaches the target temperature T0 is detected as a parameter related to the temperature T of the heater 23. Since the rate α of rise of the temperature T varies depending on the tissue volume and the degree of wetness of the treatment target, as described hereinbefore, the rate α of rise of the temperature T varies depending on the state of the treatment target including the thermal load on the treatment target. Consequently, even while the treatment tool 2 is being supplied with both the high-frequency electric power P and the heater electric power P', the state of the treatment tool can appropriately be detected by detecting the rate α of rise.

According to the present embodiment, furthermore, while the treatment target is being modified by the high-frequency current, the threshold value Zth for the impedance Z that is used to determine whether to stop the output from the high-frequency power supply 31 is set based on the detected rate α of rise of the temperature T, and the output of the high-frequency electric power P is stopped based on the arrival of the impedance Z at the threshold value Zth. Since the threshold value Zth for the impedance Z is set based on the rate α of rise, the threshold value Zth is set to an appropriate value corresponding to the state of the treatment target. Therefore, by stopping the output of the high-frequency electric power P based on the arrival of the impedance Z at the threshold value Zth, the time during which the output is produced from the high-frequency power supply 31 is of an appropriate length corresponding to the state of the treatment target. Thus, the time during which the high-frequency current is applied to the treatment target, i.e., the time during which the treatment target is modified by the heat caused by the high-frequency current applied thereto, is also of an appropriate length corresponding to the state of the treatment target. According to the present embodiment, therefore, even while the treatment tool 2 is being supplied with both the high-frequency electric power P and the heater electric power P', the output of the high-frequency electric power P is appropriately controlled based on the state of the treatment target.

Modifications

According to the first embodiment, in the output control process for controlling the output from the heater power supply 41 based on the target temperature T0, the rate α of rise of the temperature T is detected, and the threshold value Zth for the impedance Z that is used to determine whether to stop the output to the electrode 21 and 22 based on the detected rate α. However, the present disclosure is not limited to such details. According to a modification, in the output control process for controlling the output from the heater power supply 41 based on the target temperature T0, the processor 25 detects either one of the peak electric power P'p of the heater electric power P', the time Y required for the heater electric power P' to reach the peak electric power P'p, the rate γ of increase of the heater electric power P' up to the peak electric power P'p, the rate ε of reduction of the heater electric power P' after having reached the peak electric power P'p, and the integrated value W' of the heater electric power P' as a parameter related to the output to the heater 23, instead of carrying out the processing of step S104 for detecting the rate α of rise of the temperature T. The integrated value W' of the heater electric power P' may be either one of an integrated value between two points of time until the peak electric power P'p is reached, an integrated value between two points of time including the peak electric power P'p, and an integrated value between two points of time after the peak electric power P'p has been reached. The processor 25 then sets the threshold value Zth for the impedance Z that is used to determine whether to stop the output from the high-frequency power supply 31 to the electrodes 21 and 22, based on the above parameter, i.e., either one of P'p, Y, γ, ε, and W', related to the detected output to the heater 23, instead of carrying out the processing of step S105.

As described hereinbefore, since each of the peak electric power P'p, the reaching time Y, the rate γ of increase, the rate ε of reduction, and the integrated value W' varies depending on the tissue volume of the treatment target, the degree of wetness of the treatment target, etc., ease of those parameters varies depending on the state of the treatment target including the thermal load on the treatment target. However, as described hereinbefore, the larger the thermal load on the treatment target, the larger each of the parameters, i.e., P'p, Y, γ, ε, and W'. According to the present modification, therefore, the larger the parameter, i.e., either one of P'p, Y, γ, ε, and W', related to the detected output to the heater 23, the processor 25 sets the threshold value Zth for the impedance Z to a larger value. According to the present modification, the output of the high-frequency electric power supply P is stopped based on the arrival of the impedance Z at the threshold value Zth.

According to the present modification, by detecting the parameter, i.e., either one of P'p, Y, γ, ε, and W', related to the output to the heater 23, the state of the treatment target is appropriately detected even while the treatment tool 2 is being supplied with both the high-frequency electric power P and the heater electric power P'. Furthermore, as the threshold value Zth for the impedance Z is set based on the parameter, i.e., either one of P'p, Y, γ, ε, and W', the threshold value Zth is set to an appropriate value corresponding to the state of the treatment target. The output of the high-frequency electric power supply P is stopped based on the arrival of the impedance Z at the threshold value Zth. According to the present modification, therefore, the time during which the output is produced from the high-frequency power supply 31 is of an appropriate length corresponding to the state of the treatment target. Thus, the time during which the high-frequency current is applied to the treatment target, i.e., the time during which the treatment target is modified by the heat caused by the high-frequency current applied thereto, is also of an appropriate length corresponding to the state of the treatment target. According to the present modification, therefore, while the treatment tool 2 is being supplied with both the high-frequency electric power P and the heater electric power P', the output of the high-frequency electric power P is appropriately controlled based on the state of the treatment target.

According to a modification, in the output control process for controlling the output from the heater power supply 41 based on the target temperature T0, the processor 25 detects the parameter, i.e., α, related to the temperature T of the heater 23 and a plurality of ones of the parameters, i.e., P'p, Y, γ, ε, and W', related to the output to the heater 23. Then, the processor 25 sets the threshold value Zth for the impedance Z that is used to determine whether to stop the output from the high-frequency power supply 31 to the electrodes 21 and 22, based on the detected parameters, i.e., two or more of α, P'p, Y, γ, ε, and W'.

According to a modification, the processor 25 sets the threshold value Zth based on the impedance Z before the parameter, i.e., either one of α, P'p, Y, γ, ε, and W', is detected, in addition to the parameter, i.e., either one of α, P'p, Y, γ, ε, and W'. According to the present modification, the processor 25 detects the impedance Z based on the output from the high-frequency power supply 31 before the parameter, i.e., either one of α, P'p, Y, γ, ε, and W', is detected. At this time, the processor 25 detects an initial value Ze for the impedance Z at the same time as or immediately after the start of the output from the high-frequency power supply 31, and/or a chronological change of the impedance Z from the initial value Ze until the parameter, i.e., either one of α, P'p, Y, γ, ε, and W', is detected. When the threshold value Zth is to be set based on the rate α of rise of the temperature T and the chronological change of the impedance Z, for example, the threshold value Zth that is to be set is different if the impedance Z varies differently before the parameter, i.e., either one of α, P'p, Y, γ, ε, and W', is detected even though the rate α of rise remains the same.

According to the embodiment described hereinbefore, etc., the threshold value Zth for the impedance Z is used to determine whether to stop the output to the electrodes 21 and 22. However, the present disclosure is not limited to such details. According to a modification, the processor 25 sets a threshold value Qth for an output time Q of the high-frequency electric power P from the start of the output control process for controlling the output from the high-frequency power supply 31 based on the target trajectory for the impedance Z, instead of performing the processing of S105 for setting the threshold value Zth for the impedance Z. According to the present modification, the processor 25 also detects either one of the parameter, i.e., α, related to the temperature T of the heater 23 and the parameters, i.e., P'p, Y, γ, ε, and W', related to the output to the heater 23 in the output control process for controlling the output from the heater power supply 41 based on the target temperature T0. Then, the processor 25 sets the threshold value Qth for the output time Q of the high-frequency electric power P output to the electrodes 21 and 22 based on the detected parameter, i.e., either one of α, P'p, Y, γ, ε, and W'. According to the present modification, the larger the thermal load on the treatment target, the processor 25 sets the threshold value Qth for the output time Q to a longer value. Consequently, in case the rate α of rise of the temperature T is to be detected as a parameter related to the temperature T, the smaller the rate α of rise, the processor 25 sets the threshold value Qth to a longer value. If the peak electric power P'p of the heater electric power P' is to be detected as a parameter related to the output to the heater 23, then the larger the peak electric power P'p, the processor 25 sets the threshold value Qth to a longer value.

According to the present modification, the processor 25 determines whether to stop the output to the electrodes 21 and 22 using the set threshold value Qth for the output time Q, instead of the processing of S109 for determining whether to stop the output of the high-frequency electric power P based on the threshold value Zth. At this time, if the output time Q from the start of the output control process for controlling the output of the high-frequency electric power P based on the target trajectory for the impedance Z is shorter than the threshold value Qth, then the processor 25 continuously performs a process similar to the processing of S106 through S108 to continue the output to the electrodes 21 and 22, thereby continuously modifying the treatment target by applying the high-frequency current thereto. Therefore, until the output time Q reaches the threshold value Qth, i.e., until a condition based on the set threshold value Qth is satisfied, the processor 25 continues the output from the high-frequency power supply 31 to the electrodes, i.e., bipolar electrodes, 21 and 22. If the output time Q is equal to or larger than the threshold value Qth, then the processor 25 performs a process similar to S110 to stop the output from the high-frequency power supply 31 to the electrodes 21 and 22.

According to the present modification, since the threshold value Qth for the output time Q from the start of the output control process for controlling the output of the high-frequency electric power P based on the target trajectory for the impedance Z is set based on the parameters, i.e., α, P'p, Y, γ, ε, and W', the threshold value Qth is set to an appropriate value corresponding to the state of the treatment target. Therefore, by stopping the output of the high-frequency electric power P based on the arrival of the output time Q at the threshold value Qth, according to the present modification, the time during which the high-frequency current is applied to the treatment target, i.e., the time during which the treatment target is modified by the heat caused by the high-frequency current applied thereto, is also of an appropriate length corresponding to the state of the treatment target. According to the present modification, therefore, even while the treatment tool 2 is being supplied with both the high-frequency electric power P and the heater electric power P', the output of the high-frequency electric power P is also appropriately controlled based on the state of the treatment target.

According to a modification, the processor 25 sets a threshold value Qath for an output time Qa from the start of the output of the high-frequency electric power P based on the parameter, i.e., either one of α, P'p, Y, γ, ε, and W', rather than the threshold value Qth for the output time Q from the start of the output control process for controlling the output of the high-frequency electric power P based on the target trajectory for the impedance Z. Therefore, according to the embodiment in which the threshold, i.e., Qth or Qath, is set for the output time, i.e., Q or Qa, the processor 25 sets the threshold value, i.e., Qth or Qath, is set for the output time, i.e., Q or Qa from a certain point of time after the high-frequency power supply 31, based on the parameter, i.e., either one of α, P'p, Y, γ, ε, and W'.

According to a modification, the processor 25 sets both the threshold value Zth for the impedance Z and the threshold value, i.e., Qth or Qath, for the output time, i.e., Q or Qa, based on the parameter, i.e., either one of α, P'p, Y, γ, ε, and W'. According to the present modification, the processor 25 stops the output of the high-frequency electric power P based on the arrival of the impedance Z at the threshold value Zth or the arrival of the output time, i.e., Q or Qa, at the threshold value, i.e., Qth or Qath.

In the embodiment described hereinbefore, etc., the rate β of increase that is a target value is set to a fixed value β0 in the output control process for controlling the high-frequency electric power P based on the target trajectory where the impedance Z increases at the rate β of increase. However, the present disclosure is not limited to such details. According to a modification, the processor 25 sets the rate β of increase of the impedance Z according to the target trajectory based on the detected parameter, i.e., either one of α, P'p, Y, γ, ε, and W'. Then, the processor 25 sets a target trajectory for the impedance Z based on the set rate β of increase. Therefore, if the magnitude of the detected parameter, i.e., either one of α, P'p, Y, γ, ε, and W', is different, then the set target trajectory for the impedance Z is different. The larger the thermal load on the treatment target, the rate β of increase of the target trajectory is set to a larger value. Consequently, in case the rate α of rise of the temperature T is to be detected as a parameter related to the temperature T, the smaller the rate α of rise, the processor 25 sets the rate β of increase to a larger value. If the peak electric power P'p of the heater electric power P' is to be detected as a parameter related to the output to the heater 23, then the larger the peak electric power P'p, the processor 25 sets the rate β of increase to a larger value.

According to a modification, when the parameter, i.e., either one of α, P'p, Y, γ, ε, and W', is detected, the processor 25 carries out either one of a constant voltage control process for keeping the output voltage V at a constant voltage value Va, a constant power control process for keeping the output electric power from the high-frequency power supply 31, i.e., the high-frequency electric power P, at a constant electric power value Pa, and a constant current control process for keeping the output current I at a constant current value Ia, rather than performing the processing of S107 for controlling the output of the high-frequency electric power P based on the target trajectory. If the processor 25 carries out the constant voltage control process, then the processor 25 may set the voltage value Va that is a target value to a fixed value Va0 regardless of the detected parameter, i.e., either one of α, P'p, Y, γ, ε, and W'. The processor 25 may also set the voltage value Va based on the detected parameter, i.e., either one of α, P'p, Y, γ, ε, and W'. If the processor 25 is to set the voltage value Va based on the parameter, i.e., either one of α, P'p, Y, γ, ε, and W', then the larger the thermal load on the treatment target, the processor 25 sets the voltage value Va to a larger value. For example, in case the rate α of rise of the temperature T is to be detected as a parameter related to the temperature T, the smaller the rate α of rise, the processor 25 sets the voltage value Va to a larger value.

Similarly, if the processor 25 carries out the constant power control process, then the processor 25 may set the electric power value Pa that is a target value to a fixed value Pa0 regardless of the detected parameter, i.e., either one of α, P'p, Y, γ, ε, and W'. The processor 25 may also set the electric power value Pa based on the detected parameter, i.e., either one of α, P'p, Y, γ, ε, and W'. If the processor 25 is to set the electric power value Pa based on the parameter, i.e., either one of α, P'p, Y, γ, ε, and W', then the larger the thermal load on the treatment target, the processor 25 sets the electric power value Pa to a larger value. Similarly, if the processor 25 carries out the constant current control process, then the processor 25 may set the current value Ia that is a target value to a fixed value Ia0 regardless of the detected parameter, i.e., either one of α, P'p, Y, γ, ε, and W'. The processor 25 may also set the current value Ia based on the detected parameter, i.e., either one of α, P'p, Y, γ, ε, and W'. If the processor 25 is to set the current value Ia based on the parameter, i.e., either one of α, P'p, Y, γ, ε, and W', then the larger the thermal load on the treatment target, the processor 25 sets the current value Ia to a larger value. According to the present modification, at a point of time upon elapse of a certain time from the start of either one of the constant voltage control process, the constant power control process, and the constant current control process described hereinbefore, the treatment target is dehydrated to a certain extent. Therefore, after the point of time upon elapse of the certain period of time from the start of either one of the constant voltage control process, the constant power control process, and the constant current control process, the impedance Z increases chronologically due to the continuously applied high-frequency current.

According to a modification, after the parameter, i.e., either one of α, P'p, Y, γ, ε, and W', has been detected, the processor 25 switches between the constant voltage control process, the constant power control process, and the constant current control process based on the impedance Z. In this case, the processor 25 switches between the constant voltage control process, the constant power control process, and the constant current control process based on a switching valve Zs1 and a switching value Zs2 larger than the switching value Zs1. For example, if the impedance Z is smaller than the switching value Zs1, then the processor 25 carries out the above constant current control process on the output from the high-frequency power supply 31. If the impedance Z is equal to or larger than the switching value Zs1 and smaller than the switching value Zs2, then the processor 25 carries out the above constant power control process on the output from the high-frequency power supply 31. If the impedance Z is equal to or larger than the switching value Zs2, then the processor 25 carries out the above constant voltage control process on the output from the high-frequency power supply 31. According to the present modification, the threshold value Zth is set larger than the switching valve Zs1 and the switching value Zs2 if the threshold value Zth for the impedance Z is set.

According to a modification, when the parameter, i.e., either one of α, P'p, Y, γ, ε, and W', is detected, the processor 25 sets a target trajectory that increases chronologically at a constant rate η of increase for the output voltage V from the high-frequency power supply 31. Then, the processor 25 controls the output from the high-frequency power supply 31 to cause the output voltage V to change along the target trajectory. The constant rate η of increase for the output voltage V may be a fixed value η0, or may be set based on the detected parameter, i.e., either one of α, P'p, Y, γ, ε, and W'. If the rate η of increase for the output voltage V is to be set based on the parameter, i.e., either one of α, P'p, Y, γ, ε, and W', then the larger the thermal load on the treatment target, the processor 25 sets the rate η of increase that is a target value to a larger value. Moreover, there is defined a value, i.e., a starting point value, Vst of the output voltage V at the starting point of the target trajectory upon the start of the output from the high-frequency power supply 31 based on the target trajectory. According to the present modification, the value Vst of the output voltage V at the starting point of the target trajectory may be a fixed value Vst0 or may be set based on the detected parameter, i.e., either one of α, P'p, Y, γ, ε, and W'. If the value Vst of the output voltage V on the target trajectory is to be set based on the parameter, i.e., either one of α, P'p, Y, γ, ε, and W', then the larger the thermal load on the treatment target, the processor 25 sets the starting point value Vst as a target value to a larger value. According to a modification, when a predetermined condition is satisfied while the output from the high-frequency power supply 31 is being controlled based on the target trajectory where the output voltage V increases the constant rate η of increase, the processor 25 switches the output control process for controlling the output from the high-frequency power supply 31 to the constant voltage control process with the voltage value Va as described hereinbefore.

In the embodiment described hereinbefore, etc., the output from the high-frequency power supply 31 is started at the same time as or immediately after the start of the output from the heater power supply 41, and the high-frequency power supply 31 outputs the high-frequency electric power P before the parameter, i.e., either one of α, P'p, Y, γ, ε, and W', is detected. However, the present disclosure is not limited to such details. According to a modification, the processor 25 may start the output to the electrodes 21 and 22 after having started the output to the heater 23 and having detected the parameter, i.e., either one of α, P'p, Y, γ, ε, and W'. In this case, the processor 25 keeps stopping the output from the high-frequency power supply 31, instead of performing the processing of S102. According to the present modification, when the output from the high-frequency power supply 31 is started, the processor 25 controls the output from the high-frequency power supply 31 in a manner to have the impedance Z vary along the target trajectory, for example, modifying the treatment target with the high-frequency current applied thereto. According to the present modification, the processor 25 stops the output from the high-frequency power supply 31 when the above predetermined condition based on the threshold value Zth for the impedance Z or the threshold, i.e., Qth or Qath, for the output time, i.e., Q or Qa, is satisfied. In other words, the output of the high-frequency electric power P is continued, continuously modifying the treatment target with the high-frequency current applied thereto, until the above predetermined condition based on the threshold value Zth or the threshold, i.e., Qth or Qath, is satisfied.

In the embodiment described hereinbefore, etc., the output from the high-frequency power supply 31 is stopped when the predetermined condition based on the threshold value Zth for the impedance Z or the threshold, i.e., Qth or Qath, for the output time, i.e., Q or Qa, is satisfied. However, the present disclosure is not limited to such details. According to a modification, when the above predetermined condition based on the threshold value Zth for the impedance Z or the threshold, i.e., Qth or Qath, for the output time, i.e., Q or Qa, is satisfied, the processor 25 lowers the output from the high-frequency power supply 31, reducing the high-frequency current flowing through the treatment target to such an extent that the treatment target will not be modified. According to the present modification, the processor 25 stops the output from the high-frequency power supply 31 upon elapse of a certain time from the reduction of the output to the electrodes 21 and 22 or an operation made by the surgeon or the like.

In the embodiments described hereinbefore, etc., the energy output source 31 or 41 of the energy source apparatus 3 outputs high-frequency electric power P to the bipolar electrodes 21 and 22 thereby to cause a high-frequency current to flow through the treatment target between the bipolar electrodes 21 and 22, and outputs heater electric power P' to the heater 23 thereby to cause the heater 23 to generate heat. The processor 25 performs the output control process on the output to the heater 23 to cause the heater 23 to reach the target temperature T0 and to maintain the heater 23 at the target temperature T0, and detects the parameter, i.e., $\alpha$; P'p; Y; $\gamma$; $\varepsilon$; or W' related to at least one of the temperature T of the heater 23 and the output to the heater 23 in the output control process based on the target temperature T0. Then, the processor 25 sets the threshold value, i.e, Zth; Qth; or Qath that is used to determine to stop or lower the output to the bipolar electrodes 21 and 22 while the treatment target is being modified by the high-frequency current applied thereto, based on the detected parameter, i.e., $\alpha$; P'p; Y; $\gamma$; $\varepsilon$; or W'.

The present disclosure is not limited to the embodiments described hereinbefore, but various modifications may be made therein without departing from the scope of the disclosure when it is reduced to practice. The embodiments may be appropriately combined as much as possible, and the combinations offer combined advantages. Furthermore, the embodiments include disclosures in various stages, and various disclosures can be extracted by appropriately combining a plurality of components that are disclosed.

In sum, one aspect of the disclosed technology is directed to an energy source apparatus used in a treatment tool having a heater and bipolar electrodes. The energy source apparatus comprises an energy output source configured to output high-frequency electric power to the bipolar electrodes through a first circuit. A high-frequency current flows through a treatment target between the bipolar electrodes. The energy output source is configured to output heater electric power to the heater for generating heat through a second circuit. At least one processor is configured to control the energy output source. The processor is configured to control the heater for reaching a target temperature while maintaining the heater at the target temperature. The processor detects a parameter calculated based on the second circuit during the process of controlling the heater for reaching the target temperature and sets a threshold value used to determine to stop or to lower the output to the bipolar electrodes based on the parameter.

The processor is configured to start outputting the high-frequency electric power to the bipolar electrodes after outputting the heater electric power and detecting the parameter and continuously modify the treatment target by applying the high-frequency current thereto and continuing the output to the bipolar electrodes until a condition based on the threshold value is satisfied. The smaller the parameter, the processor sets the threshold value to a larger value. The processor is configured to detect a rate of increase of the temperature of the heater until the target temperature is reached as the parameter. The larger the parameter, the processor sets the threshold value to a larger value. The processor is configured to detect at least one of peak electric power of the heater electric power output to the heater, a time required for the heater electric power to reach the peak electric power, a rate of increase of the heater electric power until the peak electric power is reached, a rate of reduction of the heater electric power after the peak electric power is reached, and an integrated value of the heater electric power, as the parameter. The processor is configured to set the threshold value with respect to at least one of an impedance of the treatment target and an output time to the bipolar electrodes. The processor is configured to detect the parameter calculated based on the second circuit during the process of controlling the heater for reaching the target temperature, the parameter being related to a temperature of the heater and/or an output from the heater electric power, set a threshold value used to determine to stop or to lower the output to the bipolar electrodes based on the parameter while the treatment target is being modified by the high-frequency current applied thereto.

Another aspect of the disclosed technology is directed to a treatment system comprises a treatment tool having a heater and bipolar electrodes to grip a treatment target. An energy source apparatus is used to electrically communicate with the treatment tool. The energy output source is configured to output high-frequency electric power to the bipolar electrodes through a first circuit, a high-frequency current flowing through the treatment target between the bipolar electrodes, and the energy output source configured to output heater electric power to the heater for generating heat through a second circuit. At least one processor is used to control the energy output source. The at least one processor is configured to control the heater for reaching a target temperature while maintaining the heater at the target temperature, to detect a parameter calculated based on the second circuit during the process of controlling the heater for reaching the target temperature, and to set a threshold value used to determine to stop or to lower the output to the bipolar electrodes based on the parameter.

A further aspect of the disclosed technology is directed to a method of operating a treatment system having a treatment tool including a heater and bipolar electrodes to grip a treatment target. An energy source apparatus is used to electrically communicate with the treatment tool. The energy source apparatus comprises at least one processor used to control the energy output source by: performing an output control process on the heater electric power so that the heater reaches a target temperature and maintains the heater at the target temperature, detecting a parameter related to the heater from the heater in the output control process based on the target temperature, and setting a threshold value used to determine to stop or to lower the output to the bipolar electrodes while the treatment target is being modified by the high-frequency current applied thereto, based on the detected parameter. The processor is setting the threshold value with respect to at least one of an impedance of the treatment target and an output time to the bipolar electrodes.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. An energy source apparatus used in a treatment tool having a heater and bipolar electrodes, the energy source apparatus comprising:
   an energy output source configured to output high-frequency electric power to the bipolar electrodes through a first circuit, a high-frequency current flowing through a treatment target between the bipolar electrodes, and the energy output source is configured to output heater electric power to the heater for generating heat through a second circuit; and
   at least one processor configured to:
      control the energy output source,
      control an output of the heater electric power through the second circuit so that the heater reaches a target temperature and then maintains the heater at the target temperature,
      detect a parameter related to at least one of a temperature of the heater and the output of the heater electric power to the heater through the second circuit, the parameter including at least a rate of increase of the temperature of the heater with time, and
      set a threshold value used to stop or reduce the output of the high-frequency electric power supplied through the first circuit to the bipolar electrodes based on the detected parameter, the threshold value being set in regard to an impedance of the high-frequency electric power based on the detected rate of increase of the temperature of the heater, the threshold value of the impedance being used to stop or reduce the output of the high-frequency electric power.

2. The energy source apparatus of claim 1, wherein the processor is configured to:
   start outputting the high-frequency electric power to the bipolar electrodes after outputting the heater electric power and detecting the parameter, and
   continuously modify the treatment target by applying the high-frequency current to the treatment target, and continuing the output of the high-frequency electric power to the bipolar electrodes until a condition based on the threshold value is satisfied.

3. The energy source apparatus of claim 1, wherein the smaller a value of the parameter, the processor sets the threshold value to a larger value.

4. The energy source apparatus of claim 3, wherein the processor is configured to detect a rate of increase of the temperature of the heater until the target temperature is reached as the parameter.

5. The energy source apparatus of claim 1, wherein the larger a value of the parameter, the processor sets the threshold value to a larger value.

6. The energy source apparatus of claim 5, wherein the processor is configured to detect at least one of (i) peak electric power of the heater electric power output to the heater, (ii) a time required for the heater electric power to reach the peak electric power, (iii) a rate of increase of the heater electric power until the peak electric power is reached, (iv) a rate of reduction of the heater electric power after the peak electric power is reached, and (v) an integrated value of the heater electric power, as the parameter.

7. The energy source apparatus of claim 1, wherein the processor is configured to set the threshold value with respect to at least one of an impedance of the treatment target and an output time to the bipolar electrodes.

8. The energy source apparatus of claim 1, wherein the processor is configured to
detect the parameter further based on the second circuit during the process of controlling the heater for reaching the target temperature, the parameter being related to at least one of the temperature of the heater and the output of the heater electric power, and
set the threshold value based on the parameter while the treatment target is being modified by the high-frequency current applied to the treatment target.

9. The energy source apparatus of claim 1, wherein the processor is configured to set the threshold value of the impedance lower as the detected rate of increase of the temperature of the heater increases.

10. The energy source apparatus of claim 1, wherein the processor is configured to:
further detect, as the parameter, a rate of increase of the temperature of the heater with time; and
set the threshold value in regard to an output time of the high-frequency electric power from a start of the output based on the detected rate of increase of the temperature of the heater, the threshold value of the output time being used to stop or reduce the output of the high-frequency electric power.

11. A treatment system comprising:
a treatment tool having a heater and bipolar electrodes to grip a treatment target; and
an energy source apparatus used to electrically communicate with the treatment tool, the energy source apparatus including:
an energy output source configured to output high-frequency electric power to the bipolar electrodes through a first circuit, a high-frequency current flowing through the treatment target between the bipolar electrodes, and the energy output source is configured to output heater electric power to the heater for generating heat through a second circuit, and
at least one processor used to control the energy output source, the at least one processor being configured to:
control an output of the heater electric power through the second circuit so that the heater reaches a target temperature and then maintains the heater at the target temperature,
detect a parameter related to at least one of a temperature of the heater and the output of the heater electric power to the heater through the second circuit, the parameter including at least a rate of increase of the temperature of the heater with time, and
set a threshold value used to stop or reduce the output of the high-frequency electric power supplied through the first circuit to the bipolar electrodes based on the detected parameter, the threshold value being set in regard to an impedance of the high-frequency electric power based on the detected rate of increase of the temperature of the heater, the threshold value of the impedance being used to stop or reduce the output of the high-frequency electric power.

12. The treatment system of claim of claim 11, wherein the processor is configured to:
execute the output to the bipolar electrodes after having executed the output to the heater and having detected the parameter, and
continuously modify the treatment target by applying the high-frequency current to the treatment target and continuing the output of the high-frequency electric power to the bipolar electrodes until a condition based on the threshold value is satisfied.

13. The treatment system of claim of claim 11, wherein the smaller a value of the parameter, the processor sets the threshold value to a larger value.

14. The treatment system of claim of claim 11, wherein the larger a value of the parameter, the processor sets the threshold value to a larger value.

15. The treatment system of claim of claim 11, wherein the processor is configured to set the threshold value with respect to at least one of an impedance of the treatment target and an output time to the bipolar electrodes.

16. The treatment system of claim of claim 11, wherein the processor is configured to:
detect the parameter further based on the second circuit during the process of controlling the heater for reaching the target temperature, the parameter being related to at least one of the temperature of the heater and the output of the heater electric power, and
set the threshold value based on the parameter while the treatment target is being modified by the high-frequency current to the treatment target.

17. A method of operating a treatment system having a treatment tool including a heater and bipolar electrodes to grip a treatment target and an energy source apparatus used to electrically communicate with the treatment tool, the energy source apparatus including at least one processor used to control an energy output source, the method comprising:
performing an output control process to control an output of the heater electric power through a second circuit so that the heater reaches a target temperature and then maintains the heater at the target temperature,
detecting a parameter related to at least one of a temperature of the heater and the output of the heater electric power to the heater through the second circuit, the parameter including at least a rate of increase of the temperature of the heater with time, and
setting a threshold value used to stop or reduce the output of the high-frequency electric power supplied through a first circuit to the bipolar electrodes while the treatment target is being modified by a high-frequency current applied to the treatment target, based on the detected parameter, the threshold value being set in regard to an impedance of the high-frequency electric power based on the detected rate of increase of the temperature of the heater, the threshold value of the impedance being used to stop or reduce the output of the high-frequency electric power.

18. The method of operating the treatment system of claim 17, wherein the processor sets the threshold value based on at least one of an impedance of the treatment target and an output time to the bipolar electrodes.

\* \* \* \* \*